United States Patent
Kimbahune et al.

(10) Patent No.: US 12,274,536 B2
(45) Date of Patent: Apr. 15, 2025

(54) METHOD AND SYSTEM FOR SCREENING AND MONITORING OF CARDIAC DISEASES

(71) Applicant: Tata Consultancy Services Limited, Mumbai (IN)

(72) Inventors: Sanjay Madhukar Kimbahune, Thane (IN); Sujit Raghunath Shinde, Thane (IN); Arpan Pal, Kolkata (IN); Sundeep Khandelwal, Noida (IN); Tanuka Bhattacharjee, Kolkata (IN); Shalini Mukhopadhayay, Kolkata (IN); Rohan Banerjee, Kolkata (IN); Avik Ghose, Kolkata (IN); Tapas Chakravarty, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 308 days.

(21) Appl. No.: 16/946,718

(22) Filed: Jul. 1, 2020

(65) Prior Publication Data

US 2021/0000356 A1 Jan. 7, 2021

(30) Foreign Application Priority Data

Jul. 2, 2019 (IN) .............................. 201921026501

(51) Int. Cl.
*A61B 5/024* (2006.01)
*A61B 5/00* (2006.01)
(Continued)

(52) U.S. Cl.
CPC ........ *A61B 5/02416* (2013.01); *A61B 5/0006* (2013.01); *A61B 5/0024* (2013.01);
(Continued)

(58) Field of Classification Search
CPC . A61B 5/02416; A61B 5/0006; A61B 5/0024; A61B 5/6801; A61B 5/7275; A61B 5/7292; A61B 5/742; G06N 20/00
See application file for complete search history.

(56) References Cited

U.S. PATENT DOCUMENTS

2005/0288571 A1* 12/2005 Perkins ................. A61B 5/742
600/407
2012/0259233 A1* 10/2012 Chan ...................... A61B 5/08
600/484
(Continued)

OTHER PUBLICATIONS

Bouguila, Z. et al., (2014), "Autonomous Cardiac Diagnostic based on Synchronized ECG and PCG Signal", *Science and Technology Publications, Lda.*, 5 pages.
(Continued)

*Primary Examiner* — Alyssa M Alter
*Assistant Examiner* — Jessandra F Hough
(74) *Attorney, Agent, or Firm* — Finnegan, Henderson, Farabow, Garrett & Dunner, LLP

(57) ABSTRACT

Embodiments herein provide a system and method for screening and monitoring of cardiac diseases by analyzing acquired physiological signals. Unlike state of art approaches that consider only synchronized ECG and PPG signals for cardiac health analysis and do not consider PCG which is a critical signal for CAD analysis, the system synchronously captures physiological signals such as photo plethysmograph (PPG), phonocardiogram (PCG) and electrocardiogram (ECG) from subject(s) and builds an analytical model in the cloud for analyzing heart conditions from the captured physiological signals. The system and method provides a fusion based approach of combining the captured physiological signals such as PPG, PCG and ECG along with other details such as subject clinical information, demography information and so on. The analytical model is pretrained using ECG. PPG and PCG along with metadata associated with the subject such as demography and clinical information.

8 Claims, 11 Drawing Sheets

(51) Int. Cl.
*A61B 5/339* (2021.01)
*G06N 20/00* (2019.01)

(52) U.S. Cl.
CPC ............ *A61B 5/339* (2021.01); *A61B 5/6801* (2013.01); *A61B 5/7275* (2013.01); *A61B 5/7292* (2013.01); *A61B 5/742* (2013.01); *G06N 20/00* (2019.01)

(56) References Cited

U.S. PATENT DOCUMENTS

| | | | | |
|---|---|---|---|---|
| 2013/0076529 | A1* | 3/2013 | Reifman | A61B 5/7221 340/870.02 |
| 2014/0073976 | A1* | 3/2014 | Fonte | A61B 6/5217 600/504 |
| 2017/0293735 | A1* | 10/2017 | Itu | G16H 50/50 |
| 2018/0085012 | A1* | 3/2018 | Wei | A61B 5/0245 |
| 2018/0146922 | A1* | 5/2018 | Wang | A61B 5/6804 |
| 2018/0228444 | A1* | 8/2018 | Banerjee | G06N 7/01 |
| 2018/0306609 | A1* | 10/2018 | Agarwal | G06N 20/10 |
| 2019/0370490 | A1* | 12/2019 | Patel | G06F 21/6245 |

OTHER PUBLICATIONS

Tejedor, J. et al., (2019), "Multiple Physiological Signals Fusion Techniques for Improving Heartbeat Detection: A Review", *Sensors 2019*, 19, 4708, 34 pages.

Chakir, F. et al., (2020), "Recognition of Cardiac Abnormalities from Synchronized ECG and PCG Signals", *Science and Technology Publications, Lda*, retrieved from https://doi.org/10.1007/s13246-020-00875-2, 5 pages.

* cited by examiner

METHOD AND SYSTEM FOR SCREENING AND MONITORING OF CARDIAC DISEASES

PRIORITY CLAIM

The present application claims priority from Indian provisional patent application no. IN-201921026501, filed on Jul. 2, 2019. The entire contents of the aforementioned application are incorporated herein by reference.

TECHNICAL FIELD

The disclosure herein generally relates to field of health monitoring, and more particularly, to system and method for screening and monitoring of cardiac diseases.

BACKGROUND

In the past century, there has been a shift in the disease pattern and death pattern from communicable to non-communicable diseases with cardiovascular diseases being the number one cause. Unfortunately early stages of the disease are totally asymptomatic and are very difficult to detect by noninvasive methods and as a result most patient come to know about the presence of the disease once they have a primary event e.g. myocardial infarction (heart attack) or other complications. A large number of these patients die out of hospital and those who survive will have lifetime risk of secondary events and will have to live with complications of primary event throughout the life. Hence there is a compelling need to bring in a system and method which can noninvasively predict and aid in early diagnosis of heart diseases and put these patients on treatment path and prevent life threatening disease and its complications.

Works in literature have been researching on photo plethysmograph (PPG), phonocardiogram (PCG) and electrocardiogram (ECG) acquired from a person and analyzing them for cardiac disease predictions. However, these signals are captured asynchronously in sequential manner one after another. Multiple features are extracted from these physiological signals. Existing method analyze features of each sensed signal (PPG, PCG, ECG) of a subject under observation independently and then classify as the subject as having Coronary Artery Disease (CAD) or normal. Machine learning have been used for above classification and the output of classification is fused for the detection of CAD based on predefined criteria. However, there exists a relation among these signals, which is hardly explored for disease analysis. Thus, with existing methods focused on independent analysis of the ECG, PPG and PCG affects the accuracy of disease diagnosis. Few works in literature capture few of the physiological signals in synchronous manner for analysis however they limit to only ECG and PPG synchronization without any attempt to consider synchronously capturing other critical physiological signals which contribute towards improving accuracy of cardiac disease predictions.

SUMMARY

Embodiments of the present disclosure present technological improvements as solutions to one or more of the above-mentioned technical problems recognized by the inventors in conventional systems. For example, in one embodiment, a method for screening and monitoring cardiac diseases by analyzing acquired physiological signals, the method comprising: displaying a User Interface (UI), by one or more hardware processors of a heart sense device, for enabling entering of metadata comprising demography and clinical information associated with a subject among a plurality of subjects screened and monitored via an authenticated access to the heart sense device, wherein a plurality of probes of the heart sense device are non-invasively attached to the subject.

Further, synchronously acquiring by the one or more hardware processors via the plurality of probes, a plurality of physiological signals comprising an ECG, a PPG, and a PCG of the subject, wherein synchronously acquiring the plurality of physiological signals comprises: acquiring each of the plurality of physiological signals as a plurality of segments of data; converting the plurality of segments of data corresponding to the physiological signals into a plurality of digital segments using an Analog to Digital Converter (ADC); associating each of the plurality of digital segments with time stamps; pre-processing each of the plurality of segments with the time stamps to discard noisy segments and identify a plurality of clean segments; identifying a set of synchronous segments from the plurality of clean segments based on mapping time stamps, wherein each of the set of synchronous segments corresponds to each of the plurality of physiological signals, and wherein the set of synchronous segments are captured over a configurable predetermined time interval; and displaying the set of synchronous segments on the UI.

Furthermore, transmitting by the one or more hardware processors, the set of synchronous segments and the metadata of the subject to a cloud server via an application on a mobile device, wherein the application on the mobile device communicates with the heart sense device over a short range communication interface and enables editing of metadata and preliminary analysis on the set of synchronous segments via an authenticated access mechanism.

Furthermore, analyzing using an analytical model in the cloud server, the set of synchronous segments and the metadata of each of the plurality of subjects and predicting a cardiac disease among a plurality of cardiac diseases, wherein the analytical model is a pretrained Machine Learning (ML) model.

In another aspect, a system for screening and monitoring cardiac diseases by analyzing acquired physiological signals, the system comprising: a heart sensing device, a mobile device, and a cloud server, wherein: the heart sensing device comprises a memory storing instructions; one or more Input/Output (I/O) interfaces; and one or more hardware processors coupled to the memory via the one or more I/O interfaces, wherein the one or more hardware processors are configured by the instructions to: display a User Interface (UI) for enabling entering of metadata comprising demography and clinical information associated with a subject among a plurality of subjects screened and monitored via an authenticated access to the heart sense device, wherein a plurality of probes of the heart sense device are non-invasively attached to the subject;

Further, synchronously acquire via the plurality of probes, a plurality of physiological signals comprising an ECG, a PPG, and a PCG of the subject, wherein synchronously acquiring the plurality of physiological signals comprises: acquiring each of the plurality of physiological signals as a plurality of segments of data; converting the plurality of segments of data corresponding to the physiological signals into a plurality of digital segments using an Analog to Digital Converter (ADC); associating each of the plurality of digital segments with time stamps; pre-processing each of the plurality of segments with time stamps to discard noisy segments and identify a plurality of clean segments; identifying a set of synchronous segments from the plurality of clean segments based on mapping time stamps, wherein each of the set of synchronous segments corresponds to each of the plurality of physiological signals, and wherein the set of synchronous segments are captured over a configurable predetermined time interval; and displaying the set of synchronous segments on the UI.

Furthermore, transmit the set of synchronous segments and the metadata of the subject to a cloud server via an application on a mobile device, wherein the application on the mobile device communicates with the heart sense device over a short range communication interface and enables editing of metadata and preliminary analysis on the set of synchronous segments via an authenticated access mechanism.

Furthermore, the cloud server is configured to analyze, using an analytical model, the set of synchronous segments and the metadata of each of the plurality of subjects and predicting a cardiac disease among a plurality of cardiac diseases, wherein the analytical model is a pretrained Machine Learning (ML) model.

In yet another aspect, there are provided one or more non-transitory machine-readable information storage mediums comprising one or more instructions, which when executed by one or more hardware processors causes a method for screening and monitoring cardiac diseases by analyzing acquired physiological signals, the method comprising: displaying a User Interface (UI), by one or more hardware processors of a heart sense device, for enabling entering of metadata comprising demography and clinical information associated with a subject among a plurality of subjects screened and monitored via an authenticated access to the heart sense device, wherein a plurality of probes of the heart sense device are non-invasively attached to the subject.

Further, synchronously acquiring by the one or more hardware processors via the plurality of probes, a plurality of physiological signals comprising an ECG, a PPG, and a PCG of the subject, wherein synchronously acquiring the plurality of physiological signals comprises: acquiring each of the plurality of physiological signals as a plurality of segments of data; converting the plurality of segments of data corresponding to the physiological signals into a plurality of digital segments using an Analog to Digital Converter (ADC); associating each of the plurality of digital segments with time stamps; pre-processing each of the plurality of segments with time stamps to discard noisy segments and identify a plurality of clean segments; identifying a set of synchronous segments from the clean segments based on mapping time stamps, wherein each of the set of synchronous segments corresponds to each of the plurality of physiological signals, and wherein the set of synchronous segments are captured over a configurable predetermined time interval; and displaying the set of synchronous segments on the UI.

Furthermore, transmitting by the one or more hardware processors, the set of synchronous segments and the metadata of the subject to a cloud server via an application on a mobile device, wherein the application on the mobile device communicates with the heart sense device over a short range communication interface and enables editing of metadata and preliminary analysis on the set of synchronous segments via an authenticated access mechanism.

Furthermore, analyzing using an analytical model in the cloud server, the set of synchronous segments and the metadata of each of the plurality of subjects and predicting a cardiac disease among a plurality of cardiac diseases, wherein the analytical model is a pretrained Machine Learning (ML) model.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

Figure 1:
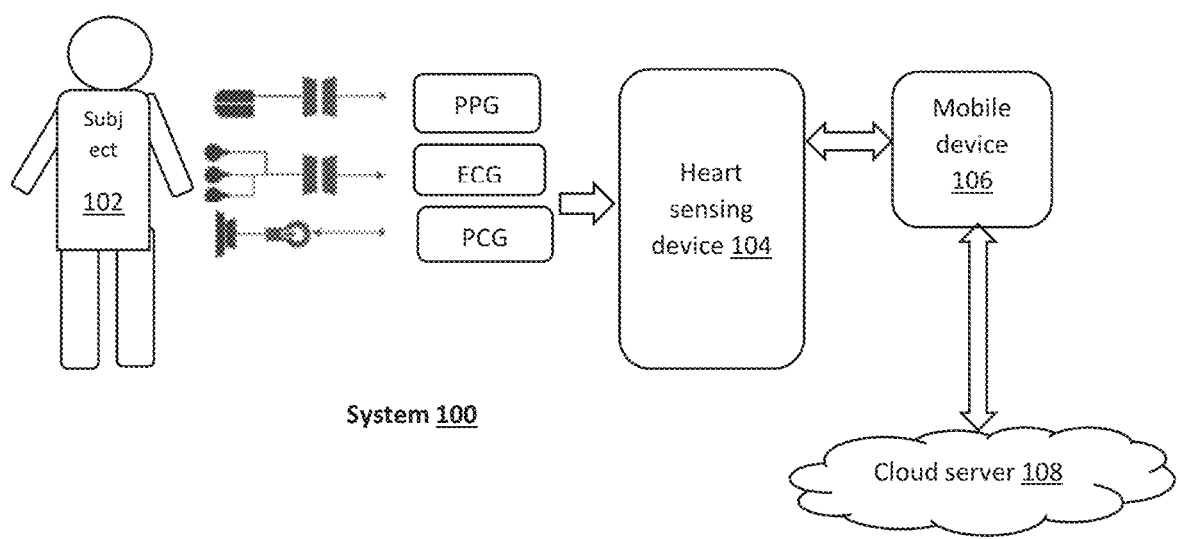
FIG. 1 illustrates an exemplary architecture of a system for screening and monitoring of cardiac diseases by analyzing acquired physiological signals, in accordance with some embodiments of the present disclosure.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION OF EMBODIMENTS

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a system and method for screening and monitoring of cardiac diseases by analyzing acquired physiological signals. The system synchronously captures physiological signals such as photo plethysmograph (PPG), phonocardiogram (PCG) and electrocardiogram (ECG) from subject(s) by synchronizing to a particular time stamp and builds an analytical model in the cloud for analyzing heart conditions from the captured physiological signals. The system and method provides a fusion based approach of combining the captured physiological signals such as PPG, PCG and ECG along with other details such as subject clinical information, demography information and so on. The analytical model is pretrained using ECG. PPG and PCG along with metadata associated with the subject such as demography and clinical information.

The heart condition or cardiac disease referred herein is Coronary Artery Disease (CAD) and the analytical models built are for CAD. However, it can be understood that the system can be modified for screening and monitoring subjects for any cardiac disease of interest that is related to the ECG, PPG and PCG signals.

Major problem associated with CAD is that the manifestations of CAD specific markers are not always guaranteed in cardiovascular signals, alternatively referred herein as physiological signals. CAD is related to the partial/complete blockage of coronary arteries. The partial blockage in the peripheral arteries can co-exist across arteries. As mentioned in literature, the basic pathological reason behind it is atherosclerosis which is a generalized process and can manifest in the PPG morphology CAD also affects the normal ECG morphology through S-T depression and inverted T wave. Stenosis in the artery causes vibration during blood flow. Although human ear cannot detect that very accurately using a stethoscope, PCG signals, recorded using high quality digital stethoscope shows high spectral power content in a region above 100 Hz. Table 1 provides a summary of the CAD related information that is expected to be derived from the sensors and metadata.

TABLE 1

| Data | Features associated with CAD |
|---|---|
| PCG | CAD patients typically have higher spectral components above 100 Hz, owing to valvular disease. Not always detected by human auditory system, can be detected by signal processing and ML |
| Single lead ECG | Morphological changes in ECG traces by CNN or other machine learning techniques. Although not always present, some discriminating patterns (e.g. Inverted T wave S-T segment depression) might be found |
| PPG | Numerous prior arts suggest HRV of CAD patient are found to be lesser. PPG can be used for unobtrusive low time HRV monitoring |
| Patient clinical and demography information (age, height, weight, BP, self and family medical history,) | Cardiac risk estimation which may lead to CAD |

However, due to many to one mapping between the disease and the sensor observation, as given in Table 2, the classification of CAD using a single marker often results in suboptimal performance. Hence the required is to do an effective combination of features extracted from multiple sensor signals using the means of ML for better accuracy.

TABLE 2

| Disease | abnormal HRV | Abnormal ECG, ST depression/ inverted T wave | Abnormal heart sound(S3 present or other high frequency components |
|---|---|---|---|
| CAD | Yes | Yes | Yes |
| AF | Yes | No | Sometimes |
| Diabetes | Yes | No | No |
| Benign cardiac murmur | No | No | Yes |
| Stress | Yes | Sometimes | No |
| COPD | Maybe | No | Yes |
| Asthma | Mostly No | Mostly No | Yes, but different pattern |

As can be in the above table 2, there are two problems with the above symptomatic analysis. Firstly, not all patients of CAD exhibit all manifestations, there is a probability associated with the each of the manifestations like HRV, ECG anomalies and abnormal sound to be caused due to the underlying condition of CAD. A true figure of prevalence for each of these markers is unknown from literature and may be demography dependent. The second problem is that several of these manifestations when taken alone can be caused by a number of different underlying conditions which may not even be of cardiac nature, like electrolyte imbalance and increased cranial pressure along with diabetes and hypertension etc.

However, referring to works in literature differential diagnosis approach can be applied to conclude that all manifestations occurring simultaneously may be caused by a single underlying condition, which reduces the search space substantially by using multiple signals of cardiac nature. Further, as mentioned in other prior work, if multiple features are taken from the signals on a large cohort of control and diseased population, a market basket analysis can be run on the space to screen a particular disease like CAD with high probability. This is also supported by study on 150 subjects, as an effective fusion of multiple sensor signal boosts up the overall sensitivity to 0.9, which is higher than any individual sensor data. Hence, there is a need for synchronized data capture of PPG, PCG and ECG on a large population of diseased patients and controls to prove the efficacy of the early screening of CAD and possibly give indications on the severity of the disease condition.

Hence, the system disclosed herein analyses multiple such cardiovascular signals by synchronous acquisition along with subject demography and clinical information, simultaneously for devising an early screening system for CAD in an individual under screening. Thus, system fuses multiple weak markers to predict more accurate CAD analysis and predictions. Unlike, existing methods that focus only on ECG and PPG, the system disclosed herein includes PCG, which is one of the critical factor for accurate CAD analysis and predictions.

Referring now to the drawings, and more particularly to FIG. 1 through FIG. 4, where similar reference characters denote corresponding features consistently throughout the figures, there are shown preferred embodiments and these embodiments are described in the context of the following exemplary system and/or method.

FIG. 1A illustrates an exemplary architecture of a system 100 for heart sensing monitoring of cardiac diseases by analyzing acquired physiological signals, in accordance with some embodiments of the present disclosure.

The architecture of system 100 comprises a heart sensing device 104 for synchronous capture of physiological signals from a subject 102 under observation. Further a mobile device 106 enables sharing of the acquired health data corresponding to the physiological signals with a cloud server 108 for analysis of the acquired health data of the subject 102 using prior built analytical models. The heart sensing device 104 enables synchronous data collection of physiological signals such as PPG, PCG, ECG from subject 102 using a set sensors attached to the subject. The acquisition of synchronous physiological signals, interchangeably referred as signals, can be performed even by a non-expert such as a general health care professional, health attendants and the like. The functions and components of the heart sensing device 104 are further explained in conjunction with FIG. 2A and FIG. 2B. The synchronous physiological signals from heart sensing device 104 are further transferred to mobile device 106 using any short range communication such as Bluetooth or the like. The mobile device 106 can serve or function as a digital platform to connect heart sensing device 104 with the cloud server 108 comprising an analytical model (not shown) for cardiac data analysis. The mobile device 106 can be any digital device such as tablet/phone, desktop and the like with an application installed, which enables communication with the heart sensing device 104. The synchronous physiological signals are further uploaded to a cloud server 108 using Wi-Fi/GSM. Further, any additional information/metadata related to the acquired signals corresponding to the subjects under screening can also be shared with the cloud server 108. The uploaded synchronous physiological signals are analyzed for any cardiac health conditions with the help of the analytical model in the cloud server. The analysis results from the analytical model are further analyzed/visualized by experts (doctors) for one or more heart diseases but not limited to such as Coronary Artery Disease (CAD), and hypertension.

The person under screening is the person who is attending the health check-up camp. The person under screening is connected to the Heart Sense Device through ECG cable, SpO2 sensor, and Digital Stethoscope.

A ECG cable is used to capture ECG signals through 3 lead or 5 lead cable. The ECG cable is connected to the person under screening through the adhesive/suction electrodes. A SpO2 sensor is connected to the patient (subject 102) for getting PPG. diaphragm of stethoscope shall be placed appropriately on chest of the subject 102 by the healthcare professional, wherein all the probe attachments or connections are non-invasive.

The Healthcare professional is a qualified person to collect human vital signs. The healthcare professional is responsible for the accurate placement of ECG electrodes, Digital Stethoscope and SpO2 probe. The Healthcare Professional is only the operator to capture the vital signs.

Figure 2A:
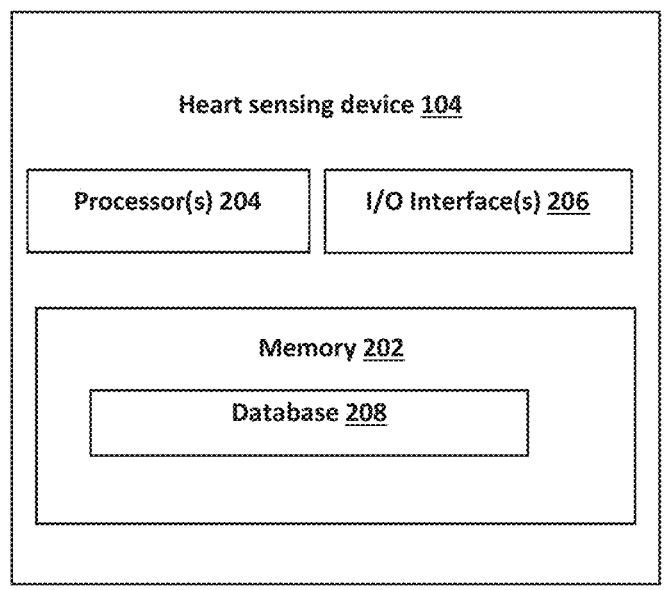
FIGS. 2A and 2B illustrates components of a heart sensing device of the system of FIG. 1 for synchronous capture of physiological signals, in accordance with some embodiments of the present disclosure.
Figure 2B:
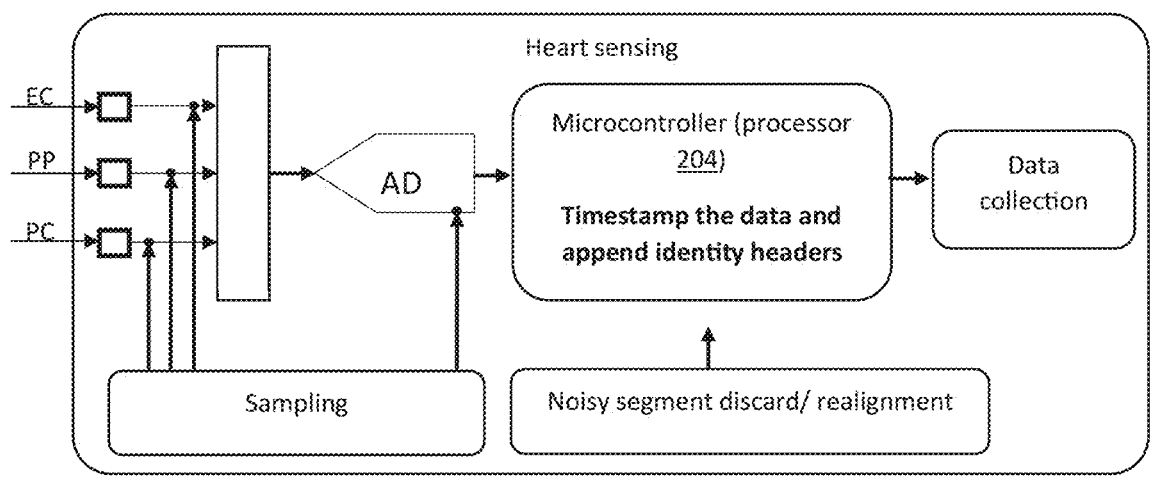
Figure 2C:
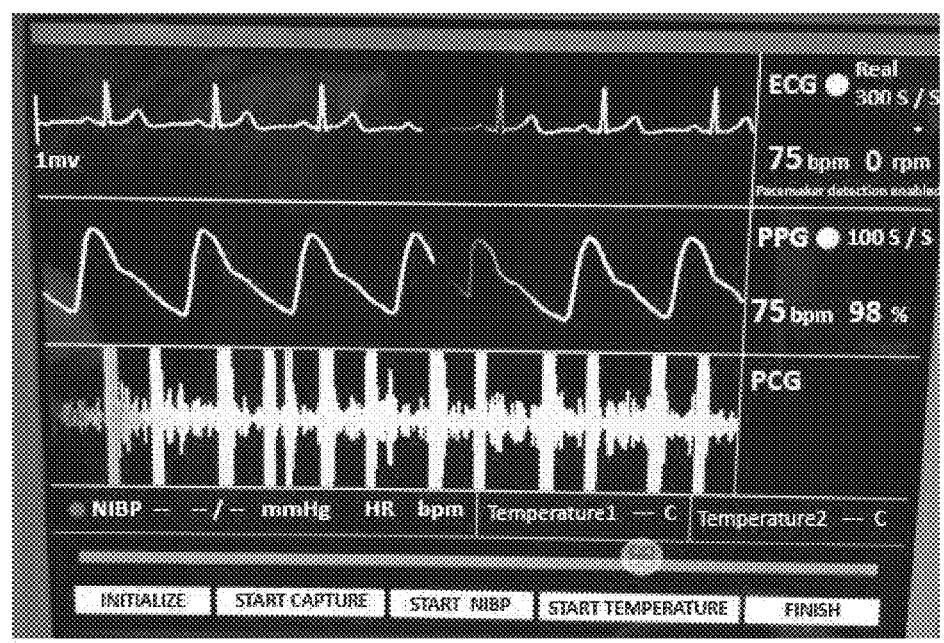
FIG. 2C-2G illustrates a real world synchronized waveforms of photo plethysmograph (PPG), phonocardiogram (PCG), and electrocardiogram (ECG) captured and displayed by the heart sensing device, in accordance with some embodiments of the present disclosure.
Figure 2D:
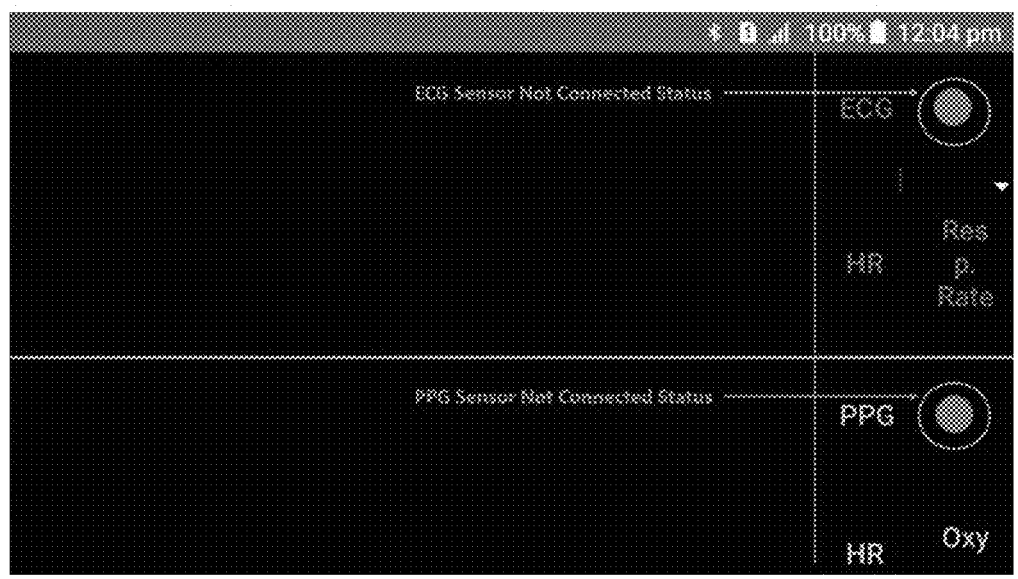
Figure 2E:
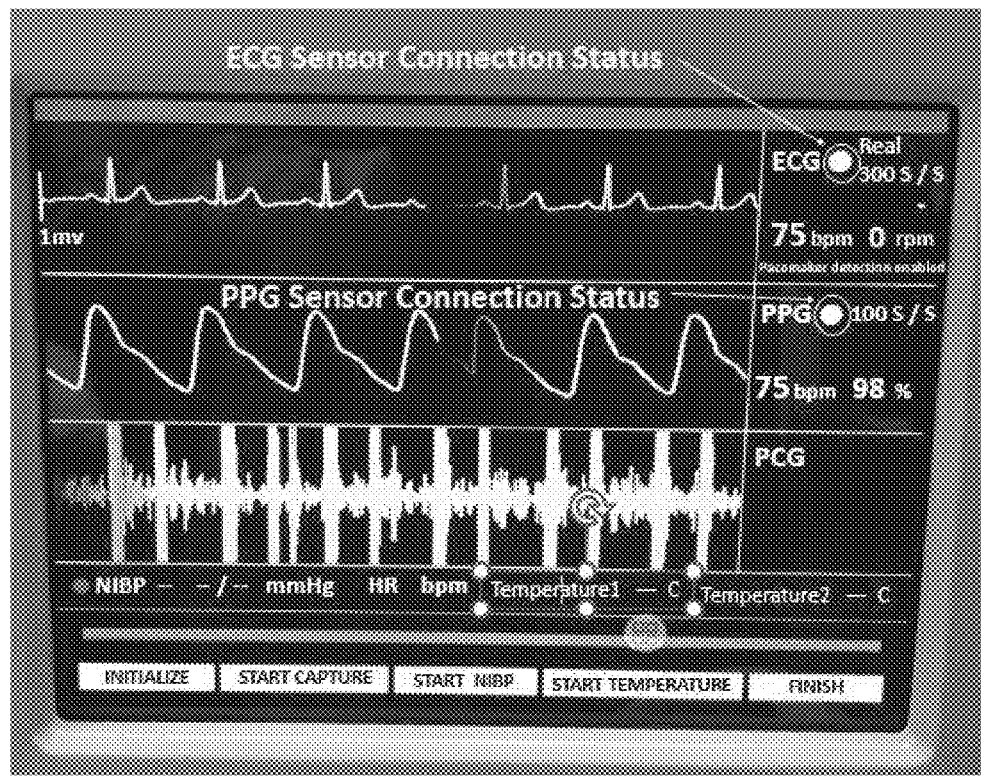
Figure 2F:
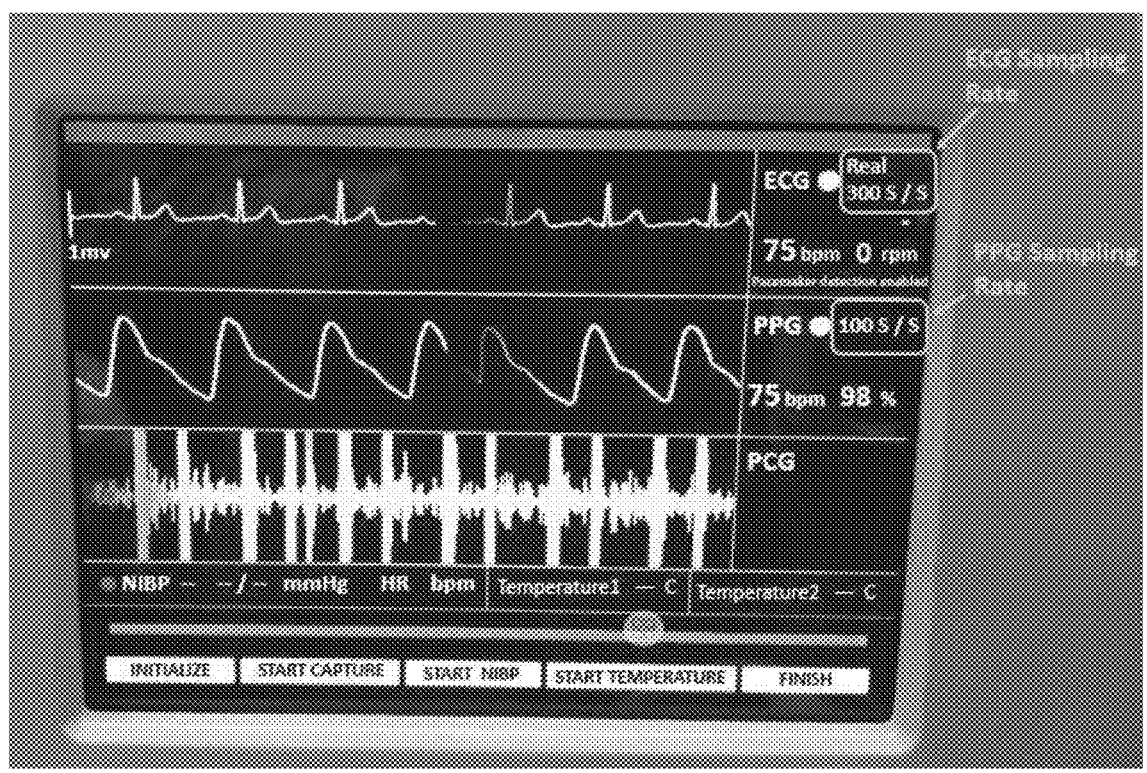
Figure 2G:
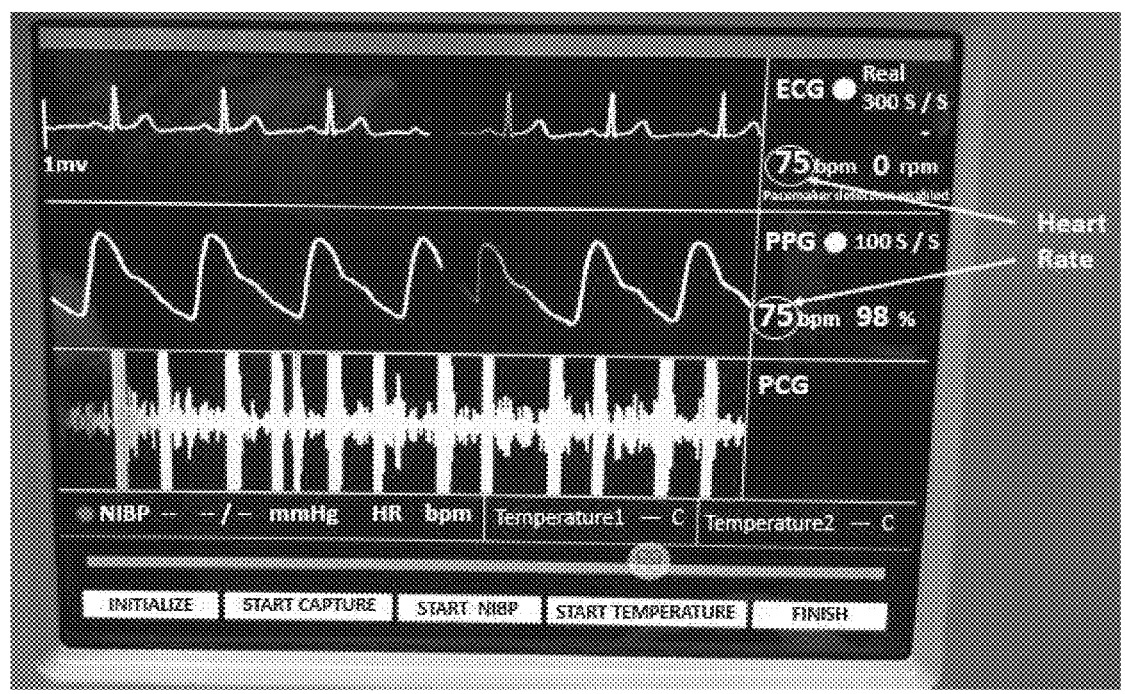

FIGS. 2A, 2B and 2C illustrate components of the heart sensing device of the system of FIG. 1 for synchronous capture of physiological signals, in accordance with some embodiments of the present disclosure.

FIG. 2A is block diagram of the heart sensing device 104. In an embodiment, the system 100 includes a processor(s) 204, communication interface device(s), alternatively referred as input/output (I/O) interface(s) 206, and one or more data storage devices or a memory 202 operatively coupled to the processor(s) 204. The heart sensing device 104 with one or more hardware processors is configured to execute functions of one or more functional blocks of the FIG. 2A. Referring to the components of heart sensing device 104, in an embodiment, the processor(s) 204, can be one or more hardware processors 204. In an embodiment, the one or more hardware processors 204 can be implemented as one or more microprocessors, microcomputers, microcontrollers (as depicted in FIG. 2B), digital signal processors, central processing units, state machines, logic circuitries, and/or any devices that manipulate signals based on operational instructions. Among other capabilities, the one or more hardware processors 204 are configured to fetch and execute computer-readable instructions stored in the memory 202. In an embodiment, the heart sensing device can be implemented in a variety of computing systems including laptop computers, notebooks, hand-held devices such as mobile phones, workstations, mainframe computers, servers, a network cloud and the like.

The I/O interface(s) 206 can include a variety of software and hardware interfaces, for example, a web interface, a graphical user interface, a touch user interface (TUI), interfaces for the ECG, PPG, PCG sensors and the like and can facilitate multiple communications within a wide variety of networks N/W and protocol types, including wired networks, for example, LAN, cable, etc., and wireless networks, such as WLAN, cellular, or satellite. In an embodiment, the I/O interface (s) 206 can include one or more ports for connecting a number of devices (nodes) of the heart sensing device to one another or to another server such as the cloud server 108 via the mobile device 106.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes.

Further, the memory 202 may include a database 208, which may store information pertaining to input(s)/output(s) of each step performed by the processor(s) 104 of the system 100 and methods of the present disclosure. For example, database may include the ECG, PPG and PCG signal samples and metadata corresponding to the subjects been monitored. In an embodiment, the database 208 may be external (not shown) to the heart sensing device 100 and coupled to the system 100 via the I/O interface 206. Functions of the components of heart sensing device 104 are explained in conjunction with FIG. 2B, 2C and flow diagram of FIGS. 3A and 3B.

FIG. 2B illustrates components of the heart sensing device 104 used by the system 100 of FIG. 1 for synchronous capture of physiological signals from a subject for monitoring of cardiac diseases, in accordance with some embodiments of the present disclosure. Three sensors ECG, PPG and PCG are connected to high speed Analog to Digital Convertor (ADC) channels. The signals from these sensors are captured in sequence with the defined sampling rates. The signals are captured via Multiplexer (MUX) and fed to the ADC. ADC shares the converted analog to digital data to a microcontroller (processor(s) 204). The Microcontroller does the noise cancellation of the signal or discards incorrect data packets based on predefined packet structure. Microcontroller adds unique current Timestamp, packets identity headers and cyclic redundancy check (CRC) around each of the data packet. Timestamped packets helps machine learning algorithms to correlate the time synchronized signals. These data packets are finally forwarded to the mobile device 106 for further processing and sharing it with the cloud server 108.

Figure 4:
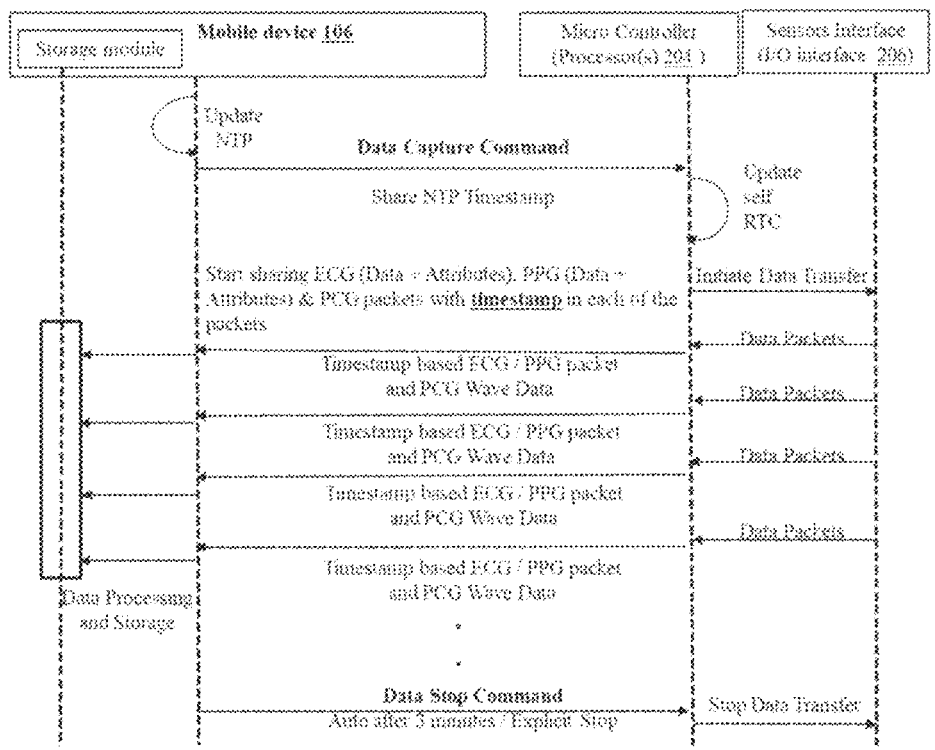
FIG. 4 illustrates data sampling and synchronization of the physiological signals, in accordance with some embodiments of the present disclosure.

The synchronous capture of the ECG, PPG and PCG is explained in conjunction with FIG. 4.

FIG. 2C-2G illustrates a real world synchronized waveforms of ECG, PPG and PCG captured and displayed by the heart sensing device 104, in accordance with some embodiments of the present disclosure. FIG. 2C-2G shows an aligned ECG/PCG and PPG waveforms on test user interface (UI) screen of the heart sensing device 104 after performing synchronization of the captured physiological signals. The heart sensing device 104 captures data with a drift of not more than 10 milliseconds. The heart sensing device 104 captures ECG signals at 300 samples per second, PPG at 100 samples per second and PCG at 8 kHz sampling rate. The heart sensing device 104 can store 1000 test data recordings of 3 minutes each and with continuous usage the device can operate around 8 hours. For ECG in resting position, it is observed post study that minimum 2 minutes of data is required for machine learning for proper screening of diseases. Hence minimum 3 minutes predefined time interval is set for data collection to improve the accuracy of predictions of the analytical model. The heart sensing device 104 is battery operated portable device, with plug in for recharging for the battery and can work in non-air condition dusty, hot and humid environments. The device comprises of a test screen user interface which displays parameters required to display test data and other vital parameters on screen. The test screen user interface comprises 3 optimal parts (shown from FIG. 2C-2G). First/major part of the test screen user interface area displays data received from PPG, PCG and ECG sensors (shown in FIG. 2C) of the subject 102. Second part of the test screen user interface area displays vital parameters such as sensors connectivity status (shown in FIG. 2D and FIG. 2E), sampling frequency (shown in FIG. 2G), pulse rate, respiration rate (FIGS. 2C and 2E), peripheral capillary oxygen saturation (SPo2) (shown in FIG. 2F) and so on. Third part of the test screen user interface provides buttons (FIG. 2C- and FIG. 2G) for user interaction to execute and save the test data.

Figure 3A:
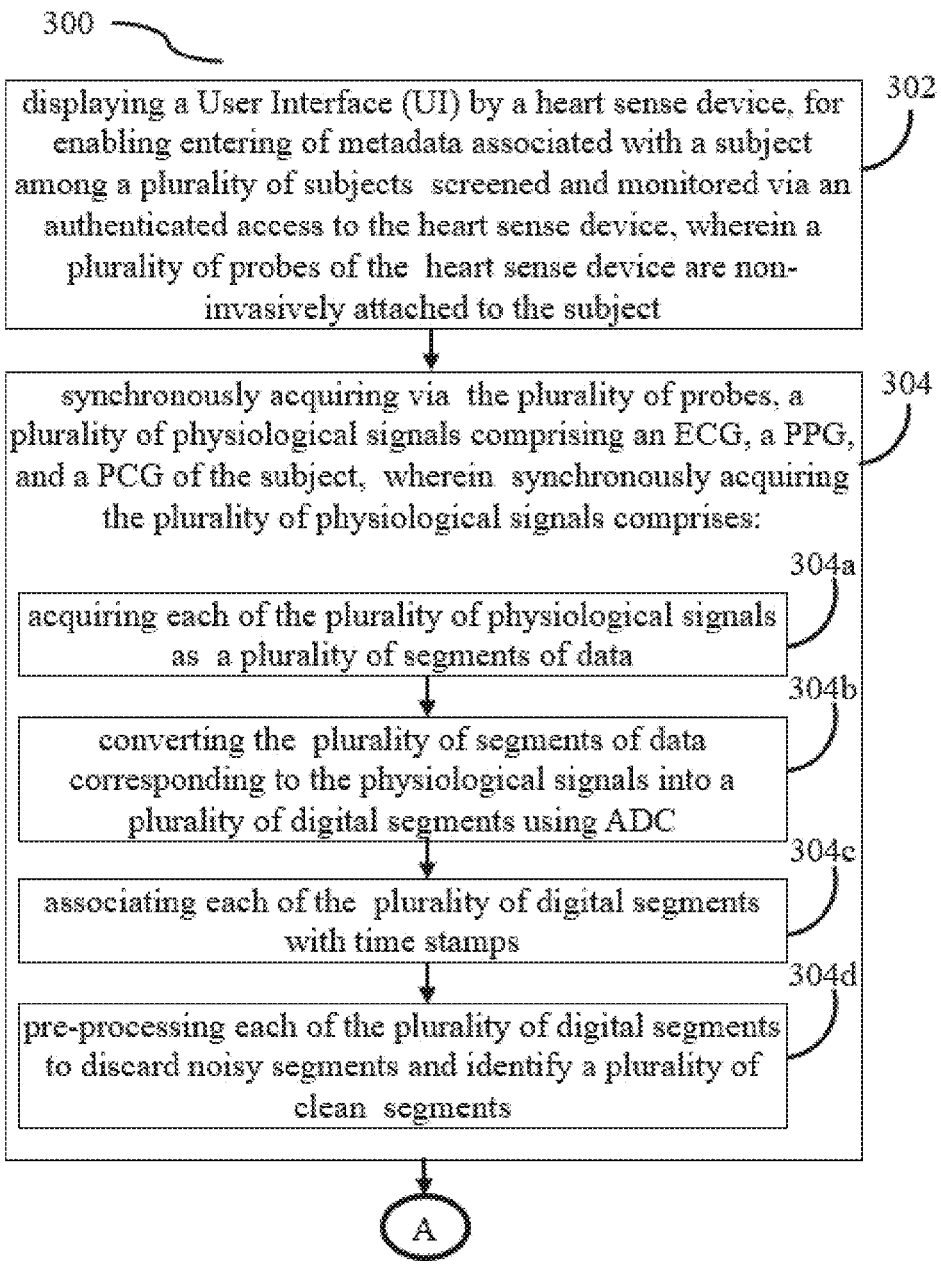
FIGS. 3A and 3B depict a flow diagram illustrating a method for screening and monitoring of cardiac diseases by analyzing acquired physiological signals using system depicted in FIG. 1, in accordance with some embodiments of the present disclosure.
Figure 3B:
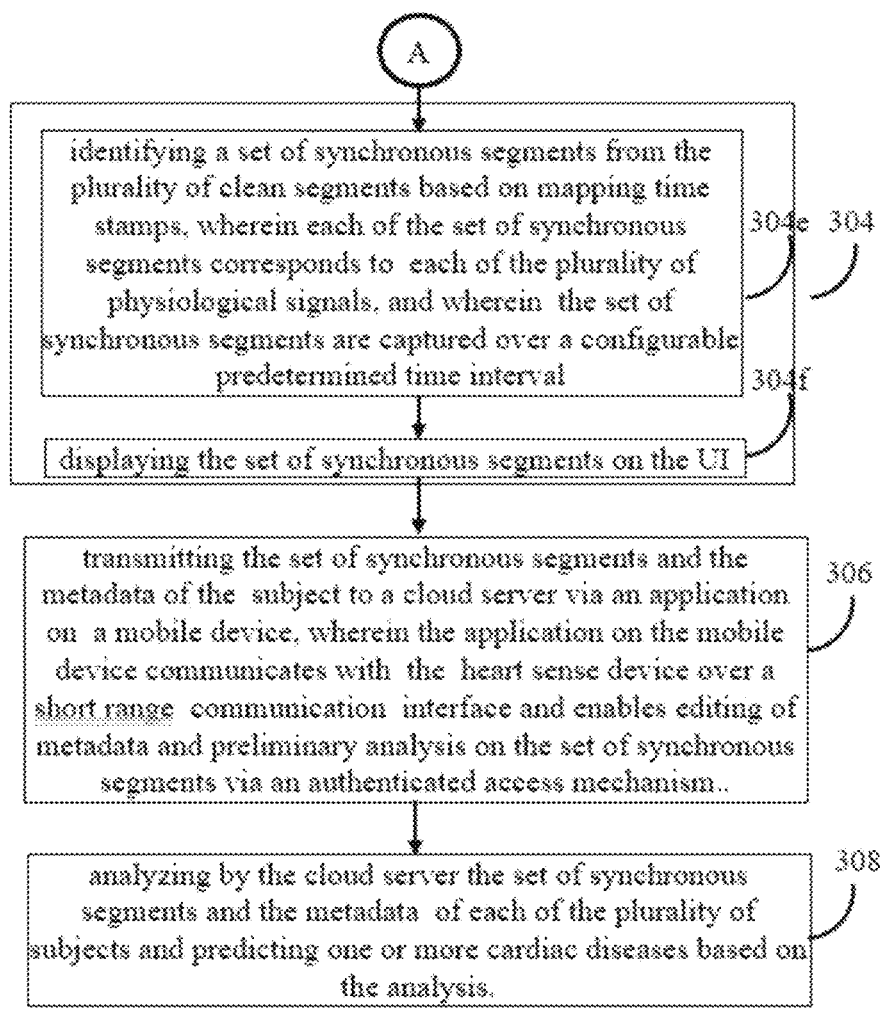

FIGS. 3A and 3B depicts a flow diagram illustrating a method 300 for screening and monitoring of cardiac diseases by analyzing acquired physiological signals using system depicted in FIG. 1, in accordance with some embodiments of the present disclosure. In an embodiment, the heart sensing device 104 comprises one or more data storage devices or the memory 202 operatively coupled to the processor(s) 204 and is configured to store instructions for execution of steps of the method 300 by the processor(s) or one or more hardware processors 204. The steps of the method 300 of the present disclosure will now be explained with reference to the components or blocks of the system 100 and the heart sensing device 104 as depicted in FIG. 1, FIG. 2A, FIG. 2B and the steps of flow diagram as depicted in FIG. 3A and FIG. 3B along with time sequence diagram for synchronization of ECG, PPG and PCG as depicted in FIG. 4. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring now to steps of method 300, at step 302 of the method 300 the one or more hardware processors (204) of the heart sensing device 104 are configured to display a User Interface (UI) for enabling entering of metadata comprising demography and clinical information associated with a subject among a plurality of subjects screened and monitored via an authenticated access to the heart sense device, wherein a plurality of probes of the heart sense device are non-invasively attached to the subject.

At step 304 of the method 300 the one or more hardware processors (204) of the heart sensing device 104 are configured to synchronously acquire via the plurality of probes, the plurality of physiological signals of the At step 304 of the method 300, the one or more hardware processors (204) are configured to subject 102, comprising an ECG, a PPG, and a PCG of the subject. The physiological signals are acquired under the supervision of the health care professional, who is responsible for the accurate placement of sensors. The heart sensing device 104 acquires heart sound through e-Stethoscope. For listening the sound, heart sensing device 104 provides an option of connecting a headphone. It provides the healthcare professional to listen the sound as in e-Stethoscope. The acquired physiological signals per person will have 3 minutes recording (configurable timings).

Synchronously acquiring the plurality of physiological signals is in accordance to the explanation as provided in the hardware of the heart sensing device 104 as explained in conjunction with FIGS. 2B and 2C. The steps for synchronous acquisition of ECG, PPG and PCG comprise:

a) acquiring each of the plurality of physiological signals as a plurality of segments of data (304 *a*).

b) converting the plurality of segments of data corresponding to the physiological signals into a plurality of digital segments using an Analog to Digital Converter (ADC) (304 *b*).

c) associating each of the plurality of digital segments, interchangeably referred herein as packets with time stamps (304 *c*).

d) Pre-processing each of the time stamped plurality of segments to discard noisy segments and identify clean segments (304 *d*). The noise cancellation of the signal or discards incorrect data packets (noisy segments) based on predefined packet structure.

e) Identifying a set of synchronous segments from the clean segments based on mapping time stamps, wherein each of the set of synchronous segments corresponds to each of the plurality of physiological signals as explained in conjunction with FIG. 2B, and wherein the set of synchronous segments are captured over a configurable predetermined time interval (304 *e*). For example, the interval may be 3 minutes window.

f) Displaying the set of synchronous segments on the UI (304 *f*) as depicted in FIG. 2C-FIG. 2G.

At step 306 of the method 300, the one or more hardware processors (204) are configured to transmit the set of synchronous segments and the metadata of the subject to a cloud server via an application on the mobile device 106. The application on the mobile device 106 communicates with the heart sense device 104 over a short range communication interface. Further, the application enables editing of metadata and preliminary analysis on the set of synchronous segments via an authenticated access mechanism.

The synchronous physiological signals are collected on the mobile device 106 which can be a digital device such as tablet/phone, desktop and so on connected via Bluetooth or wired connection to the heart sensing device 104. The collected synchronous physiological signals are uploaded to the cloud server 108 using Wi-Fi/GSM. The mobile device 106 comprises a splash screen, login screen, subject list screen, add new subject screen, subject's metadata, subject data capture screen and admin screen. The splash screen contains a logo screen for the heart sensing device 104. All users of the application can login by entering username and password details in the login screen of the mobile device 106. The health care professional can view the details of the subject under consideration in the subject list screen. The health care professional can add or modify information into the subject list using the add new subject screen and also modify the subject metadata if needed. Using the data capture screen, the health care professional can capture the physiological signals PPG, PCG and ECG of the subject and automatically upload the captured signals to the cloud server 108 for further analysis for heart health conditions. Admin screen is loaded after the login screen. Admin credentials are separate from normal user/healthcare professional. Admin screen provides an option to reset the board to factory settings or modify the board configurations. Health care professionals are not provided with admin privileges.

At step 308 of the method 300, the one or more hardware processors (204) are configured to use the analytical model in the cloud server, the set of synchronous segments and the metadata of each of the plurality of subjects and predicting a cardiac disease such as CAD among a plurality of cardiac diseases, The analytical model is a pretrained Machine Learning (ML) model. The method utilizes multiple techniques for analyzing the synchronously captured signals for determining several cardiac health conditions. Cardiac abnormality detection is performed based on the physiological signals. Physiological signals like PPG, PCG and ECG are band-limited for normal subjects. The signatures of abnormalities in the signals mostly appear in terms of spectral components, beyond that region and mostly in the higher frequency zones (e.g. murmur, arrhythmias, and CAD). A one class classifier is designed to check whether the acquired physiological signals are normal. If the acquired physiological signals are not normal, they are further analyzed for specific heart diseases.

The method proposed generates a plurality of features from the captured physiological signals PPG, PCG and ECG of the subject 102. A plurality of relevant features are extracted from the generated plurality of features by applying a set of statistical measures such as mean, variance, and kurtosis. The relevant features extracted are classified using algorithms to further analyze the various heart health conditions of the subject 102. The analysis results are provided to specialists/doctors for analyses/visualize. The specialist/ doctor can view the results using a web console. Using the web console the specialist/doctor can do the analyses/visualize the results for CAD status, and hypertension and other cardiac issues.

For example a junior doctor determines a risk score by querying the subject 102 under observation with relevant questions. If the risk score determined is high, the authenticated health care professional captures the physiological signals of the subject with the help of the heart sensing device 104. The captured signals are uploaded to the analytical model in the cloud server 108 are encrypted at the time of uploading for ensuring security. The cloud server 108 has an authentication method for receiving the uploaded signal data. A senior doctor analyzes the results of the analysis from the analytical model of the cloud server along with the risk score for any heart health conditions. Further, the analysis results are stored in memory for future analysis/visualization of the results by the doctors or experts. Thus, system disclosed herein enables:
  a. Visualization of data for a physician in such a way that he can quickly point out anomalies (marking S1. S2, R peaks etc)
  b. Ability for doctor to mark notes for further algorithm improvement

[Interpretable AI]

FIG. 4 illustrates data sampling and synchronization of the physiological signals, in accordance with some embodiments of the present disclosure. The FIG. 4 depicts a sequence data diagram for synchronous capture of ECG, PPG and PCG using an Network Time Protocol (NTP) available on the mobile device 106. Before the synchronous capture is initiated the mobile device 106 triggered by the application is configured to first update the device time with the Network Time Protocol (NTP). Whenever data capture event is initiated, mobile device 106 shares the NTP based Timestamp to microcontroller (processor 204) of the heart sensing device 104 to updates the clock time of the microcontroller. After updating the time value, microcontroller triggers start data command to sensors interface (I/O interface 206) to share the sensors data. Sensors interface shares the data in a predefined format and sampling frequency. Microcontroller adds unique Current Timestamp, packets identity headers and cyclic redundancy check (CRC) around each of the data packet. These data packets (segments) are finally forwarded to mobile device 106 for further processing and storage. The data is collected around 3 minutes and data capture auto terminates after 3 minutes or if explicit instruction of terminate data capture event are provided by the end user (health professional) performed by the user.

Table 3 below depicts example sampling frequency values used for the ECG, PPG and PCG signals.

TABLE 3

|     | Sampling Frequency | Bytes received per Second | Average time required for each sample |
| --- | --- | --- | --- |
| ECG | 300 Samples/Sec | (1 to 7 bytes length depending upon channel (1 to 7) selection) 1 * 300 samples = 300 bytes/Second . . . 7 * 300 samples = 2100 bytes/Second | 3.3 millisecond |
| PPG | 100 Samples/Sec | 100 bytes/Second | 10 millisecond |
| PCG | Audio Recording Setting: 8000 Hz, Mono Channel, 16 bit PCM | Audio Data in Wave Format | — |

As depicted from the table for ECG signal processing, usually 250 Hz sampling rate is highly acceptable, hence the heart sensing device 104 is set to 300 Hz sampling rate for ECG. ECG signals supports single or multi-channel data using heart sense device 104. Channels include I, II, III, aVR, aVL, aVF and C1. Each of the channel data is represented by a single byte value. If only single channel is used for ECG data capture, then almost 300 data bytes are received per second and for multi-channel, data size is in multiples of channels selected.

For PPG signal, 60 Hz is standard sampling rate, hence the heart sensing device 104 is set to 100 Hz sampling rate for PPG. PPG data value is represented by a single byte value. Each second 100 bytes of data are received.

For PCG the heart sensing device 104 is set to 8 KHz sampling rate with audio properties of 16-bit mono PCM data format. The sound data generated using this properties is good enough for machine learning.

Along with each of the data bytes unique timestamp, data byte identifier and cyclic redundancy check (CRC) packets are appended.

As mentioned earlier, for ECG in resting position, it is observed post study that minimum 2 minutes of data is required for machine learning for proper screening of diseases. Hence minimum 3 minutes predefined time interval is set for data collection to improve the accuracy of predictions of the analytical model.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means, and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for screening and monitoring a plurality of cardiac diseases, the method comprising:
   building an analytical model in a cloud server by synchronously capturing a first set of physiological signals, the first set of physiological signals comprising a electrocardiogram (ECG) signal, a photo plethysmograph signal (PPG) and a phonocardiogram (PCG) signal, wherein the analytical model is pretrained using the ECG signal, the PPG signal and the PCG signal along with metadata associated with a subject, and
   the first set physiological signals is synchronized to a particular time stamp;
   displaying a User Interface (UI), by one or more hardware processors of a heart sense device;
   enabling, based on the displayed UI, entering of metadata comprising demography information and clinical information, wherein
   the demography information and the clinical information are associated with a subject among a plurality of subjects,
   the subject is screened and monitored via an authenticated access to the heart sense device, and
   the heart sense device includes a plurality of probes that are non-invasively attached to the subject;
   updating a time of the heart sense device with a Network Time Protocol (NTP);
   synchronously acquiring, based on the update of the time of the heart sense device, by the one or more hardware processors via the plurality of probes, a second set of physiological signals, wherein
   the second set of physiological signals is synchronously acquired for a duration of at least 3 minutes,
   the displayed UI includes three parts that includes:
   a first part that includes test screen user interface area that displays the acquired second set of physiological signals,
   a second part that displays vital parameters, wherein the vital parameters include a sensor connectivity status, a sampling frequency of the acquired second set of physiological signals, a pulse rate of the subject, a peripheral capillary oxygen saturation (SPo2) of the subject, and
a third part includes a plurality of buttons configured for user interaction;
wherein synchronously acquiring the second set of physiological signals comprises:
a) synchronously acquiring each of the second set of physiological signals as a plurality of segments of data, wherein
each of the second set of physiological signals are synchronized to a time stamp, and
the second set of physiological signals is synchronized to a time stamp in a predefined format at a predefined sampling frequency;
b) converting the plurality of segments of data into a plurality of digital segments using an Analog to Digital Converter (ADC);
c) associating each of the plurality of digital segments with time stamps, wherein the time stamped digital segments helps machine learning models to correlate the time synchronized signals;
d) pre-processing each of the plurality of digital segments with the time stamps to discard noisy segments and identify a plurality of clean segments;
e) identifying a set of synchronous segments from the plurality of clean segments, based on mapping time stamps, wherein each of the set of synchronous segments corresponds to each of the second set of physiological signals, and wherein the set of synchronous segments are captured over a configurable predetermined time interval; and
f) displaying the set of synchronous segments on the UI;
adding a unique time stamp, packet identity headers, and a cyclic redundancy check (CRC) around each of the set of synchronous segments;
transmitting, by the one or more hardware processors, the set of synchronous segments and the metadata of the subject to the cloud server via an application on a mobile device, wherein the application on the mobile device communicates with the heart sense device over a short range communication interface and enables editing of metadata and preliminary analysis on the set of synchronous segments via an authenticated access mechanism;
generating a plurality of features from the set of synchronous segments;
extracting relevant features from the generated plurality of features by applying a set of statistical measures that includes a mean, a variance, and a kurtosis;
analyzing using the built analytical model in the cloud server, the set of synchronous segments, the extracted relevant features, and the metadata of each of the plurality of subjects; and
predicting, based on the analysis, a cardiac disease among the plurality of cardiac diseases, wherein
the cardiac disease is Coronary Artery Disease (CAD), the built analytical model is a pre-trained Machine Learning (ML) model, and the built analytical model analyzes the set of synchronous segments along with clinical information and demographic information associated with the subject to identify the cardiac disease, wherein a cardiac abnormality is classified as the cardiac disease, if the segments of the synchronously acquired physiological signals, appear in higher frequency zones and classified as not normal; and
the built analytical model is trained by synchronizing a plurality of sample physiological signals to the particular time stamp, wherein the synchronous capturing of the ECG signal, the PPG signal and the PCG signal using the NTP available on the mobile device comprises:
configuring the mobile device triggered by the application to first update a mobile device time with the NTP, before initiating synchronous capture,
whenever data capture event is initiated, sharing by the mobile device a NTP based timestamp to the hardware processor of the heart sensing device to update a clock time of the hardware processor and after updating the clock time, triggering by the hardware processor a start data command to an input/output (I/O) interface to share sensor data and sharing by the I/O interface the data in a predefined format and sampling frequency, adding an unique current timestamp, packets identity headers and a cyclic redundancy check (CRC) around each of a data packet and forwarding the data packet to the mobile device for further processing, storage, and sharing with the cloud server.

2. The method of claim 1, further comprises displaying the predicted cardiac disease on the mobile device.

3. The method of claim 1, wherein the heart sense device is a portable battery operated device.

4. A system for screening and monitoring a plurality of cardiac diseases, the system comprising:
a heart sensing device;
a mobile device; and
a cloud server; wherein the heart sensing device comprises:
a memory storing instructions;
one or more Input/Output (I/O) interfaces; and
one or more hardware processors coupled to the memory via the one or more I/O interfaces, wherein the one or more hardware processors are configured by the instructions to:
build an analytical model in a cloud server by synchronously capturing a first set of physiological signals, the first set of physiological signals comprising a electrocardiogram (ECG) signal, a photo plethysmograph signal (PPG) and a phonocardiogram (PCG) signal,
wherein the analytical model is pretrained using the ECG signal, the PPG signal and the PCG signal along with metadata associated with a subject, wherein
the first set of physiological signals is synchronized to a particular time stamp;
display a User Interface (UI);
enable, based on the displayed UI, entering of metadata comprising demography information and clinical information, wherein
the demography information and the clinical information are associated with a subject among a plurality of subjects,
the subject is screened and monitored via an authenticated access to the heart sensing device, and
the heart sensing device includes a plurality of probes that are non-invasively attached to the subject;
update a time of the heart sense device with a Network Time Protocol (NTP);
synchronously, based on the update of the time of the heart sense device, acquire via the plurality of probes, a second set of physiological signals, wherein the second set of physiological signals is synchronously acquired for a duration of at least 3 minutes, the displayed UI includes three parts that includes:
  a first part that includes test screen user interface area that displays the acquired second set of physiological signals,
  a second part that displays vital parameters, wherein the vital parameters include a sensor connectivity status, a sampling frequency of the acquired plurality of physiological signals, a pulse rate of the subject, a peripheral capillary oxygen saturation (SPo2) of the subject, and
  a third part includes a plurality of buttons configured for user interaction;
wherein synchronously acquiring the second set of physiological signals comprises:
a) synchronously acquiring each of the plurality of physiological signals as a plurality of segments of data wherein
  each of the second set of physiological signals are synchronized to a time stamp, and
  the plurality of physiological signals is synchronized to a time stamp in a predefined format at a predefined sampling frequency;
b) converting the plurality of segments of data into a plurality of digital segments using an Analog to Digital Converter (ADC);
c) associating each of the plurality of digital segments with time stamps, wherein the time stamped digital segments helps machine learning models to correlate the time synchronized signals;
d) pre-processing each of the plurality of digital segments associated with the time stamps to discard noisy segments and identify a plurality of clean segments;
e) identifying a set of synchronous segments from the plurality of clean segments based on mapping time stamps, wherein each of the set of synchronous segments corresponds to each of the second set of physiological signals, and wherein the set of synchronous segments are captured over a configurable predetermined time interval; and
f) displaying the set of synchronous segments on the UI; and
add a unique time stamp, packet identity headers, and a cyclic redundancy check (CRC) around each of the set of synchronous segments;
transmit the set of synchronous segments and the metadata of the subject to the cloud server via an application on a mobile device, wherein the application on the mobile device communicates with the heart sensing device over a short range communication interface and enables editing of metadata and preliminary analysis on the set of synchronous segments via an authenticated access mechanism; and
generate a plurality of features from the set of synchronous segments;
extract relevant features from the generated plurality of features by applying a set of statistical measures that includes a mean, a variance, and a kurtosis, wherein the cloud server configured to:
analyze using the built analytical model in the cloud server, the set of synchronous segments, the extracted relevant features, and the metadata of each of the plurality of subjects; and
predict, based on the analysis, a cardiac disease among the plurality of cardiac diseases, wherein
  the cardiac disease is Coronary Artery Disease (CAD), the built analytical model is a pre-trained Machine Learning (ML) model, and the built analytical model analyzes the set of synchronous segments along with clinical information and demographic information associated with the subject to identify the cardiac disease, wherein a cardiac abnormality is classified as the cardiac disease, if the segments of the synchronously acquired physiological signals appear in higher frequency zones and classified as not normal; and
the built analytical model is trained by synchronizing a plurality of sample physiological signals to the particular time stamp, wherein the synchronous capturing of the ECG signal, the PPG signal and the PCG signal using the NTP available on the mobile device comprises:
configuring the mobile device triggered by the application to first update a mobile device time with the NTP, before initiating synchronous capture,
  whenever data capture event is initiated, sharing by the mobile device a NTP based timestamp to the hardware processor of the heart sensing device to update a clock time of the hardware processor and after updating the clock time, triggering by the hardware processor a start data command to the I/O interface to share sensor data and sharing by the I/O interface the data in a predefined format and sampling frequency, adding an unique current timestamp, packets identity headers and a cyclic redundancy check (CRC) around each of a data packet and forwarding the data packet to the mobile device for further processing, storage, and sharing with the cloud server.

5. The system of claim 4, wherein
the cloud server is further configured to communicate the predicted cardiac disease to the mobile device, and
the mobile device is configured to display the predicted cardiac disease on the mobile device.

6. The system of claim 4, wherein the heart sensing device is a portable battery operated device.

7. One or more non-transitory machine-readable information storage mediums comprising one or more instructions, which when executed by one or more hardware processors causes a method for screening and monitoring a plurality of cardiac diseases, the method comprising:
building an analytical model in a cloud server by synchronously capturing a first set of physiological signals, the first set of physiological signals comprising a electrocardiogram (ECG) signal, a photo plethysmograph signal (PPG) and a phonocardiogram (PCG) signal, wherein the analytical model is pretrained using the ECG signal, the PPG signal and the PCG signal along with metadata associated with a subject, wherein the first set of physiological signals is synchronized to a particular time stamp;
displaying a User Interface (UI);
enabling, based on the displayed UI, entering of metadata comprising demography information and clinical information, wherein
  the demography information and the clinical information are associated with a subject among a plurality of subjects,
  the subject is screened and monitored via an authenticated access to a heart sense device, and the heart sense device includes a plurality of probes that are non-invasively attached to the subject;
updating a time of the heart sense device with a Network Time Protocol (NTP);
synchronously, based on the update of the time of the heart sense device, acquiring via the plurality of probes, a second set of physiological signals, wherein
the second set of physiological signals is synchronously acquired for a duration of at least 3 minutes,
the displayed UI includes three parts that includes:
a first part that includes test screen user interface area that displays the acquired second set of physiological signals,
a second part that displays vital parameters, wherein the vital parameters include a sensor connectivity status, a sampling frequency of the acquired plurality of physiological signals, a pulse rate of the subject, a peripheral capillary oxygen saturation (SPo2) of the subject, and
a third part includes a plurality of buttons configured for user interaction;
wherein synchronously acquiring the second set of physiological signals comprises:
a) synchronously acquiring each of the second set of physiological signals as a plurality of segments of data, wherein
each of the second set of physiological signals are synchronized to a specific time stamp, and
the second set of physiological signals is synchronized to a specific time stamp in a predefined format at a predefined sampling frequency;
b) converting the plurality of segments of data into a plurality of digital segments using an Analog to Digital Converter (ADC);
c) associating each of the plurality of digital segments with time stamps, wherein the time stamped digital segments helps machine learning models to correlate the time synchronized signals;
d) pre-processing each of the plurality of digital segments with the time stamps to discard noisy segments and identify a plurality of clean segments;
e) identifying a set of synchronous segments from the plurality of clean segments, based on mapping time stamps, wherein each of the set of synchronous segments corresponds to each of the second set of physiological signals, and wherein the set of synchronous segments are captured over a configurable predetermined time interval; and
f) displaying the set of synchronous segments on the UI; and
adding a unique time stamp, packet identity headers, and cyclic redundancy check (CRC) around each of the set of synchronous segments;
transmitting the set of synchronous segments and the metadata of the subject to the cloud server via an application on a mobile device, wherein the application on the mobile device communicates with the heart sense device over a short range communication interface and enables editing of metadata and preliminary analysis on the set of synchronous segments via an authenticated access mechanism;
generating a plurality of features from the set of synchronous segments;
extracting relevant features from the generated plurality of features by applying a set of statistical measures that includes a mean, a variance, and a kurtosis;
analyzing using the built analytical model in the cloud server, the set of synchronous segments, the extracted relevant features, and the metadata of each of the plurality of subjects; and
predicting, based on the analysis, a cardiac disease among the plurality of cardiac diseases, wherein
the built analytical model is a pre-trained Machine Learning (ML) model, and the built analytical model analyzes the set of synchronous segments along with clinical information and demographic information associated with the subject to identify the cardiac disease, wherein a cardiac abnormality is classified as the cardiac disease, if the segments of the synchronously acquired physiological signals appear in higher frequency zones and classified as not normal; and
the built analytical model is trained by synchronizing a plurality of sample physiological signals to a synchronous time stamp, wherein the plurality of specific sample physiological signals includes an PPG sample signal, an PCG sample signal, and an ECG sample signal, wherein the synchronous capturing of the ECG signal, the PPG signal and the PCG signal using the NTP available on the mobile device comprises:
configuring the mobile device triggered by the application to first update a mobile device time with the NTP, before initiating synchronous capture,
whenever data capture event is initiated, sharing by the mobile device a NTP based timestamp to the hardware processor of the heart sensing device to update a clock time of the hardware processor and after updating the clock time, triggering by the hardware processor a start data command to an input/output (I/O) interface to share sensor data and sharing by the I/O interface the data in a predefined format and sampling frequency, adding an unique current timestamp, packets identity headers and a cyclic redundancy check (CRC) around each of a data packet and forwarding the data packet to the mobile device for further processing, storage, and sharing with the cloud server.

8. The method of claim 1, wherein the heart sense device captures the ECG at 300 samples per second, the PPG at 100 samples per second, and the PCG at 8 kHz samples per second.

* * * * *